(12) United States Patent
Weber

(10) Patent No.: US 6,517,888 B1
(45) Date of Patent: Feb. 11, 2003

(54) METHOD FOR MANUFACTURING A MEDICAL DEVICE HAVING A COATED PORTION BY LASER ABLATION

(75) Inventor: Jan Weber, Tuam (IR)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/724,503

(22) Filed: Nov. 28, 2000

(51) Int. Cl.[7] .................... A61L 27/04; A61L 27/00; A61L 27/06; A61L 27/28; B05D 3/06

(52) U.S. Cl. .............. 427/2.24; 427/2.28; 427/2.1; 427/553; 427/554; 427/555; 427/556; 427/307; 427/256; 427/287

(58) Field of Search ............... 427/2.24, 2.28, 427/2.1, 553, 554, 555, 556, 307, 230, 239, 256, 287

(56) References Cited

U.S. PATENT DOCUMENTS

| | | |
|---|---|---|
| 4,655,771 A | 4/1987 | Wallsten |
| 4,733,665 A | 3/1988 | Palmaz |
| 4,800,882 A | 1/1989 | Gianturco |

(List continued on next page.)

FOREIGN PATENT DOCUMENTS

| | | | |
|---|---|---|---|
| EP | 0 689 807 A2 | 1/1996 | ............. A61F/2/06 |
| EP | 0 842 729 A1 | 5/1998 | ............ B23K/26/00 |
| EP | 0 951 877 A2 | 10/1999 | ............. A61F/2/06 |
| WO | WO95/03083 | 2/1995 | |
| WO | WO 00/54704 | 9/2000 | ............. A61F/2/06 |

OTHER PUBLICATIONS

C. Momma et al., Laser Cutting of Alotted Tube Coronary Stents—State–of–the–Art and Future Developments, Progr. Biomed. Res. 39 (Feb. 1999) pp. 39–44.*

C. Momma et al., *Beam delivery of femtosecond laser radiation by diffractive optical elements*, Appl.Phys. A 67, 517–520 (1998).

S. Nolte et al., *Polarization effects in ultrashort–pulse laser drilling*, Appl.Phys. A 68, 563–567 (1999).

M.D. Perry et al., *Ultrashort–Pulse Laser Machining*, Section K–ICALEO 1998, pp. 1–20.

C. Momma et al., *Laser Cutting of Alotted Tube Coronary Stents—State–of–the–Art and Future Developments*, Progr. Biomed.Res. 39, (Feb. 1999) pp. 39–44.

S. Nolte et al., *Micromachining with femtosecond lasers*, CLEO'98 pp. 510–511.

Laser Zentrum Hanover e.V.'s brochure on *Femtosecond Laser Micromaching*.

C. Momma et al., *Precise laser ablation with femtosecond pulses*, CLEO'97 pp. 160–161.

(List continued on next page.)

*Primary Examiner*—Shrive P. Beck
*Assistant Examiner*—Jennifer Kolb Michener
(74) *Attorney, Agent, or Firm*—Pennie & Edmonds LLP

(57) ABSTRACT

The present invention is directed to a method for manufacturing a medical device having a coated portion which comprises obtaining a structure having an inner surface and an outer surface; coating at least a portion of the inner or outer surface with a first coating material; and ablating the coated tubular structure with a laser to form at least one opening therein to form the coated portion. A plate can be used instead of the structure, and the plate is folded to form the structure after the ablation. A plurality of medical devices, made of any materials and having uniform coating (s), can be easily manufactured by the method of the present invention.

31 Claims, 2 Drawing Sheets

U.S. PATENT DOCUMENTS

| | | | |
|---|---|---|---|
| 4,886,062 A | | 12/1989 | Wictor |
| 4,954,126 A | | 9/1990 | Wallsten |
| 5,061,275 A | | 10/1991 | Wallsten et al. |
| 5,120,322 A | | 6/1992 | Davis et al. |
| 5,304,121 A | | 4/1994 | Sahatjian |
| 5,336,518 A | | 8/1994 | Narayanan et al. |
| 5,356,433 A | | 10/1994 | Rowland et al. |
| 5,464,650 A | | 11/1995 | Berg et al. |
| 5,780,807 A | * | 7/1998 | Saunders ............... 219/121.71 |
| 5,879,697 A | | 3/1999 | Ding et al. |
| 6,066,168 A | * | 5/2000 | Lau et al. .................. 623/1.16 |
| 6,096,070 A | | 8/2000 | Ragheb et al. |
| 6,153,252 A | * | 11/2000 | Hossainy et al. ............ 427/2.3 |
| 6,160,240 A | | 12/2000 | Momma et al. |

OTHER PUBLICATIONS

A.P. Kanavin et al., *Heat transport in metals irradiated by ultrashort laser pulses*, Phys. Rev. vol. 57 (23), pp. 14698–14703.

C. Momma et al., *Precise laser ablation with ultrashort pulses*, Appl. Surf. Sci. 109/110, 15–19 (1997).

B.N. Chickhov et al., *Femtosecond, picosecond and nanosecond laser ablation of solids*, Appl. Phys. A 63, 109–115 (1996).

S. Nolte et al., *Ablation of metals by ultrashort laser pulses*, J. Opt., Soc. Am. B/vol. 14 No. 10/Oct. 1997, pp. 2716–2722.

J. Kruger et al. *Femtosecond–pulse laser ablation of dental hydroxyapatite and single–crystalline fluoroaoatite*, Appl. Phys. A 69 [Suppl.] S403–407 (1999).

H.K. Tohshoff et al., *Microdrilling of metals with ultrashort laser pulses*, Journal of Laser Applications, vol. 12 (1) (Feb. 2000), pp. 23–27.

Zhu et al., Influence of laser parameters and material properties on micro drilling with femtosecond laser pulse, Appl. Phys. A 69 [Suppl.] S367–S371 (1999).

Kruger et al., Femtosecond–pulse laser ablation of dental hydroxyapatite and single–crystalline fluoroapatite, Appl. Phys. A 69 [Suppl.] S403–S407 (1999).

International Search Report for PCT/US01/44301.

* cited by examiner

US 6,517,888 B1

METHOD FOR MANUFACTURING A MEDICAL DEVICE HAVING A COATED PORTION BY LASER ABLATION

FIELD OF THE INVENTION

This invention relates generally to a method for manufacturing a medical device. More particularly, the invention is directed to a method for manufacturing a medical device having a coated portion by laser ablation.

BACKGROUND OF THE INVENTION

Implantable medical devices, such as prosthesis or stents, are used to reduce restenosis after balloon angioplasty or other procedures involving catheters. Usually, the suitable medical device or stent is cylindrical in shape. The walls of the cylindrical structure can be formed of metal or polymer with openings therein, e.g., a mesh. The stent is implanted into a body lumen, such as a blood vessel, where it stays permanently, to keep the vessel open and to improve blood flow to the heart muscle and relieve symptoms. Stents can also be positioned in other parts of the body, such as the kidneys or the brain. The stent procedure is fairly common, and various types of stents have been developed and actually used. However, since the bare metal surface of the stents may trigger restenosis, the stent surface should be altered to make it more biocompatible. Stents coated with polymers have been offered to reduce likelihood of restenosis caused by the metal surface of stents. Further, there are various types of polymer coats for stents which contain drugs which are delivered to an afflicted area of a body lumen. Drugs may be either bonded chemically, physically or absorbed in the polymer matrix. Also, for the purpose of obtaining drug delivery stents, the drugs may be directly coated or immobilized onto the stents, e.g. using a binding molecule between the drug molecule and the stent surface.

Previously, such coated stents have been manufactured by shaping the body of the stents first by photo-etching, laser ablation, electron beam ablation, or any other means, and then coating the stents with polymer compositions or drug compositions by dip-coating, spray-coating or any other means. However, due to the complex geometry of the stent, applying an even coating on a metal stent is very difficult. Therefore, methods for easily manufacturing a stent with uniform coating(s) are necessary.

In addition, the polymer coating, when applied by methods in the art, tends to create bridges at small gaps or corners between stent struts. Also, in the conventional methods, wherein a coating process takes place after a shaping process, it is almost impossible to selectively coat the stent. For example, it is impossible to coat one side of a stent without coating the other side or to apply different coatings to the outside and inside of a stent. Therefore, there is a need for methods of making a stent, especially coated stent, wherein the coating(s) does not form bridges at gaps or corners, and wherein selective coating of the stent can be readily achieved.

SUMMARY OF THE INVENTION

These and other objectives are accomplished by the present invention. To achieve the aforementioned objectives, a method has been invented for manufacturing a medical device having a coated portion by laser ablation.

An embodiment of the present invention is a method for manufacturing a medical device having a coated portion which comprises obtaining a structure having an inner surface and an outer surface. At least a portion of the inner or outer surface is coated with a first coating material. Then, the coated structure is ablated with a laser to form at least one opening therein to form the coated portion.

In another embodiment of the present invention, the method for manufacturing a medical device having a coated portion comprises obtaining a plate having a first surface and a second surface. At least a portion of the first surface or second surface is coated with a first coating material. The coated plate is then ablated with a laser to form at least one opening in the coated plate. Afterward, the coated and ablated plate is formed by folding or shaping into the medical device.

DESCRIPTION OF THE FIGURES

FIG. 1A depicts a cross-sectional view of a tubular structure.

FIG. 1B depicts a cross-sectional view of the tubular structure after a coating is applied on its inner surface.

FIG. 1C depicts a cross-sectional view of the tubular structure after another coating is applied on its outer surface.

FIG. 1D depicts a cross-sectional view of a coated tube-like portion of a medical device formed by ablating the tubular structure with a laser.

FIG. 2A depicts a cross-sectional view of a plate.

FIG. 2B depicts a cross-sectional view of the plate after a coating is applied on its first surface.

FIG. 2C depicts a cross-sectional view of the plate after another coating is applied on its second surface.

FIG. 2D depicts a cross-sectional view of the coated plate after laser ablation.

FIG. 2E depicts a cross-sectional view of a coated tube-like portion of a medical device made by forming the ablated plate into a desired shape.

DESCRIPTION OF THE PREFERRED EMBODIMENTS

Figure 1A:
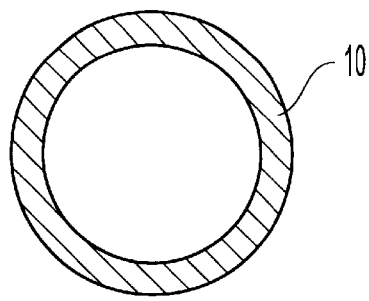
FIGS. 1A through 1D show the steps of an embodiment of the present invention.

In a method of the present invention, a structure or a plate is coated first, and then, ablated by a laser to form openings. Such ablation may be conducted with a ultrashort-pulse laser. "Ultrashort-pulse lasers" refer to lasers (light amplification by stimulated emission of radiation) consisting of pulses with durations shorter than about 10 pico ($=10^{-11}$) second. The ultrashort-pulse laser is clearly distinguished from conventional continuous wave and long-pulse lasers (nanosecond ($10^{-9}$ sec) laser) which have significantly longer pulses.

When a material is ablated by a conventional laser, the material is removed by thermal ablation wherein the material is locally heated to near melting point or boiling point. Thus, ablation using conventional lasers has various problems. For example, the ablation is furthermore accompanied by a heat transfer and a strong thermal shock to surrounding material which might cause serious damage, such as cracking. Also, the material once removed tends to redeposit or re-solidify on the surrounding surface. Thus, a material ablated by a conventional laser must be cleaned to remove the redeposited material surrounding the cut surface. Hence, if a material having an immobilized molecule on its surface is ablated by a conventional laser, because a clearing step is required, the immobilized molecule may be washed away at the cleaning step. Also, since process parameters for a conventional laser ablation, such as boiling point and absorption of the laser light, varies according to materials to be ablated, a layered material consisting of layers made of different materials cannot be ablated by a conventional laser.

On the other hand, ablation using an ultrashort-pulse laser is free from such problems. The ultrashort-pulse deposits its energy so quickly that it does not interact at all with the plume of vaporized material, which would distort and bend the incoming beam and produce a rough-edged cut. The plasma plume leaves the surface very rapidly, ensuring that it is well beyond the cut edges before the arrival of the next laser pulse. Since the pulse is very short, atoms in a material to be ablated are stationary in space with respect to the pulse duration. As a result, the ultrashort-pulse laser does not react differently between dielectric materials and electric materials. Thus, any material, including glasses, polymers, ceramics, silicon, and metals, can be ablated with very high precision without damage in surrounding area by ultrashort-pulse lasers due to the absence of heat shock waves. In addition, the surface ablated with a ultrashort-pulse laser has an excellent quality which does not need further polishing as required for a surface ablated with a conventional laser because redeposition is less or absent.

The lasers suitable for use in the method of the present invention are preferably ultrashort-pulse lasers consisting of pulses shorter than about $10^{-11}$ second, preferably shorter than about $10^{-12}$ second, and most preferably shorter than about $10^{-13}$ second which are referred to as femtosecond lasers. The ultrashort-pulse laser used for the The intensity (fluence) of the laser radiation that is required to ablate a material is dependent on the material to be ablated. Specifically each material has its own laser-induced optical breakdown (LIOB) threshold which characterizes the fluence required to ablate the material at a particular pulse width. Also the fluence of the ultrashort-pulse laser suitable for the present invention can be chosen according to the thickness of the tube wall, the thickness of the coating and each material. Furthermore, the number of pulses needed to ablate completely through a material can be calculated for a given energy or fluence.

For example, a hole without any redeposition can be drilled into a 0.7 mm-thick stainless steel plate coated with a 0.3 mm-thick poly(ethylene terephthalate) coating on its one surface, using a laser with a pulse duration of 220 femtosecond and a fluence of 0.6 $J/cm^2$ at a wavelength of 780 nm with a repetition rate of 1 kHz commercial femtosecond Ti:sapphire laser and amplifier system (SPECTRA-PHYSICS, SPITFIRE). As another example, a hole without any redeposition can be drilled into a 0.7 mm-thick piece of tantalum with a 0.3 mm-thick poly(ethylene oxide)/poly (butylene terephthalate) copolymer coating using a laser with a pulse duration of 120 femtosecond and a fluence of 0.5 $J/cm^2$ with the same system used above.

The laser ablation of the present invention can be conducted using any additional techniques for improved accuracy and efficiency of such ultrashort-pulse laser ablation, e.g. diffractive optical elements (DOEs) and/or polarization trepanning. See C. Momma et al., *Beam delivery offemtosecond laser radiation by diffractive optical elements*, Appl. Phys. A 67, 517–520 (1998); S. Nolte et al., *Polarization effects in ultrashort-pulse laser drilling*, Appl. Phys. A 68, 563–567 (1999), both are incorporated herein by reference.

The ultrashort-pulse-lasers-are known to artisans. For example, they are thoroughly disclosed by M. D. Perry et al. in *Ultrashort-Pulse Laser Machining, Section* K-ICALEO 1998, pp.1–20, which is incorporated herein by reference.

Figure 1B:
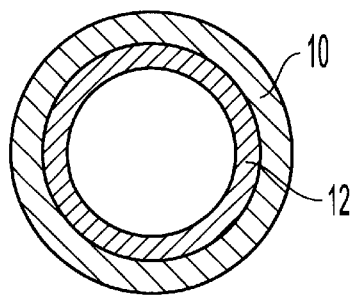
Figure 1C:
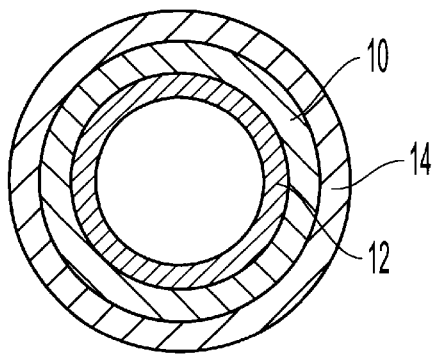
Figure 1D:
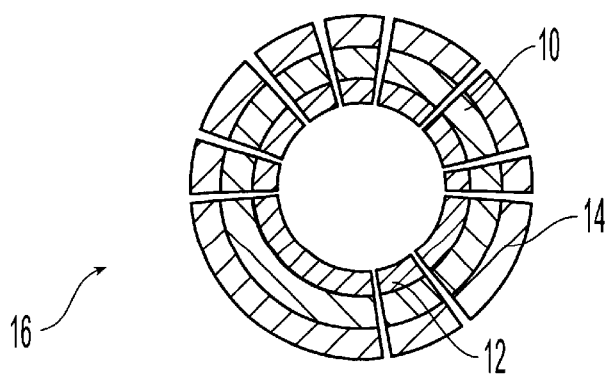

An embodiment of the present invention is illustrated in FIGS. 1A–1D in which a tubular structure made of a suitable medical device material is coated with a coating material or composition. FIG. 1A depicts a cross-sectional view of a tubular structure 10 made of a suitable medical device material. The inner surface of the tubular structure 10 is coated with first coating material or composition 12 (FIG. 1B). Then, the outer surface of the tubular structure 10 is also coated with second coating material or composition 14 (FIG. 1C) which can be the same as the first coating material or composition. The tubular structure 10 having an inner coating 12 and outer coating 14 is ablated by an ultrashort-pulse laser to form openings that made up a geometric pattern in the tubular structure (FIG. 1D). In this manner, a coated tube-like portion of a medical device 16 is formed. Alternatively, only one of the surfaces, e.g. inner or outer, may be coated.

Figure 2A:
FIGS. 2A through 2E show steps of another embodiment of the present invention.
Figure 2B:
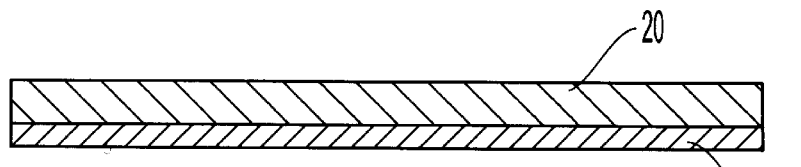
Figure 2C:
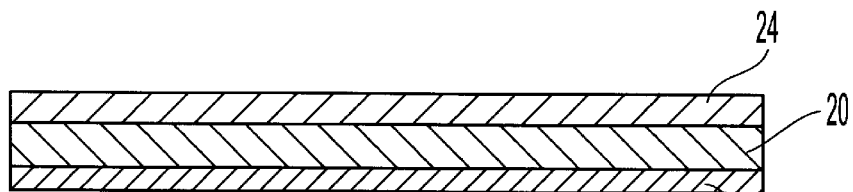
Figure 2D:
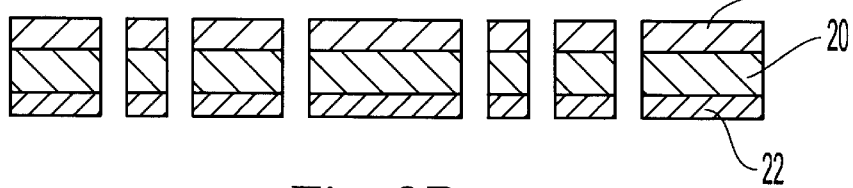
Figure 2E:
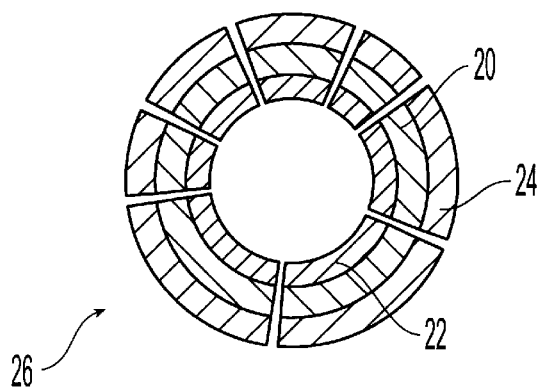

Another embodiment is illustrated in FIGS. 2A–2E. FIG. 2A depicts a cross-sectional view of a plate 20 made of a suitable medical device material. A first surface of the plate 20 is coated with first coating material or composition 22 (FIG. 2B). Then, the second surface of the plate 20 is also coated with second coating material or composition 24, which can be the same as the first coating material or composition (FIG. 2C). The plate 20 having first coating 22 and second coating 24 is ablated by an ultrashort-pulse laser to form openings that make up a geometric pattern (FIG. 2D). The plate is then folded into a desired shape to form a coated tube-like portion of a medical device 26.

The term "structure" used in relation to a medical device means any structure which is at least a part of a medical device, such as a tubular structure. Likewise, the term "coated portion" used in relation to a medical device means any portion of a medical device which has (a) coating(s) on its surface(s). An example of such coated portion is a coated tube-like portion. Medical devices that can be fabricated by the method of the present invention includes those that include a tube-like or cylindrical-like portion. The tube-like portion of the medical device need not to be completely cylindrical. For instance, the cross-section of the tube-like portion can be any shape, such as rectangle, a triangle, etc., not just a circle. Such devices include, without limitation, stents and grafts. A bifurcated stent is also included among the medical devices which can be fabricated by the method of the present invention.

Preferably, the medical device is a stent. Stents suitable for the present invention include vascular stents such as self-expanding stents and balloon expandable stents. Examples of self-expanding stents are illustrated in U.S. Pat. Nos. 4,655,771 and 4,954,126 issued to Wallsten and 5,061,275 issued to Wallsten et al. Examples of appropriate balloon-expandable stents are shown in U.S. Pat. No. 4,733,665 issued to Palmaz, U.S. Pat. No. 4,800,882 issued to Gianturco and U.S. Pat. No. 4,886,062 issued to Wiktor.

Appropriate materials for making the medical device are not limited for the present invention, and any material including ceramics, polymers and metals can be used for manufacturing the device by the method of the present invention. Preferably, the device is made of a biocompatible material. Examples for such polymers include poly(ethylene terephthalate), polyacetal, poly(lactic acid), poly(ethylene oxide)/poly(butylene terephthalate) copolymer, and polycarbonate. Examples for such metals include titanium, stainless steel, platinum, tantalum or gold/platinum alloy.

In the present invention, the term "coating" encompasses all ways of coating, such as using plasma, dipping, spraying, etching, covering, plating, co-extruding and all modern chemical ways of attaching bio-molecules to surfaces as well as conventional coating. The surface is coated with a material by a method known to the artisans, such as dipping into a polymer, spraying a coating composition onto the surface, or attaching bio-molecules to surfaces. The surface of the structure or plate is optionally subjected to a pre-treatment, such as roughing, oxidizing or adding a primer, and then coated. Adding a primer is preferable as such pre-treatment. In another embodiment, the structure or plate can be covered with a film. Further, in another embodiment, the structure or plate can be made by co-extrusion of the medical device material and the coating material. More than one coating method can be used to make a medical device. Thickness of coatings can range from almost a single layer of molecules to about 0.1 mm. Suitable thickness as of the coating are known in the art and can be selected by artisans.

Medical devices coating materials suitable for the present invention include any coating material for the stent which are known to the skilled artisan. Suitable coating materials include, without limitation, metals, such as tantalum, stainless steel, nitinol, titanium, and alloys, polymeric materials, such as poly-L-lactic acid, polycarbonate, polyethylene terephtalate, silicones, polyurethanes, thermoplastic elastomers, ethylene vinyl acetate copolymers, polyolefin elastomers, hydrogels and EPDM rubbers. Such coatings include biologically active molecules, such as heparine or insuline molecules, directly attached to oxide molecules on the surface of the structure as explained below.

Also, the coating can be a drug-releasing coating which immediately or gradually releases a biologically active material. Coating polymer useful for drug coating includes hydrogel polymers which are often used to contain the biologically active material and are disclosed in U.S. Pat. No. 5,304,121, U.S. Pat. No. 5,464,650, PCT publication WO95/03083 and U.S. Pat. No. 5,120,322, which are incorporated by reference. However, a non-hydrogel can be also used. Although polymeric molecules can be combined with biologically active molecules, biologically active materials can be directly immobilized on the surface. As disclosed in U.S. Pat. No. 5,356,433 to Rowland et al., polysaccharides can be immobilized to metallic surfaces by applying an organosilane coating with amine functionality and then applying a polysaccharide using carbodlimide as a coupling gent. U.S. Pat. No. 5,336,518 to Narayanan et al. also discloses that a polysaccharide can be immobilized on a surface by applying a coat of heptafluorobutylmethacrylate (HFBMA) by radiofrequency (RF) plasma deposition, creating functional groups on the surface by RF plasma with water vapor, and then applying the polysaccharide using carbodiimide. Moreover, examples of medical devices, in particular, stents coated with polymer/biologically active material coatings are described in U.S. Pat. No. 5,879,697 which is incorporated herein by reference.

The term "biologically active material" encompasses therapeutic agents, such as drugs, and also genetic materials and biological materials. The genetic materials mean DNA or RNA, including, without limitation, of DNA/RNA encoding a useful protein stated below, intended to be inserted into a human body including viral vectors and non-viral vectors. Viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Non-viral vectors include artificial chromosomes and mini-chromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor α and β, platelet derived endothelial growth factor, platelet derived growth factor, tumor necrosis factor α, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

Biologically active material also includes non-genetic therapeutic agents, such as:
  anti-thrombogenic agents such as heparin, heparin dervatives, urokinase, and PPack (dextrophenylalanine proline arginine chloromethylketone);
  anti-proliferative agents such as enoxaprin, angiopeptin, or monoclonal antibodies capable of blocking smooth muscle cell proliferation, hirudin, and acetylsalicylic acid, amlodipine and doxazosin;
  anti-inflammatory agents such as glucocorticoids, betamethasone, dexamethasone, prednisolone, corticosterone, budesonide, estrogen, sulfasalazine, and mesalamine;
  antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives;
  anesthetic agents such as lidocaine, bupivacaine, and ropivacaine;
  anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;
  vascular cell growth promotors such as growth factors, Vascular Endothelial Growth Factors (FEGF, all types including VEGF-2), growth factor receptors, transcriptional activators, and translational promotors;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

In the devices made by the method of the invention, both surfaces of the tube-like portion can be coated with a same material at the same time.

Also, one surface of the structure or plate need not be coated, while the other surface has a coating. A medical device having such portion is preferable for a drug-delivery medical device for delivering a biologically active material to a blood vessel surface while minimizing the amount of biologically active material which is delivered into the blood stream. Such a medical device is also preferable when the coating is easily damaged during implantation of the medical device, e.g., because of the unfolding shear-action of the delivery balloon.

Further in another embodiment, inner and outer surfaces of the portion of the medical device can be coated with different materials. For example, a stent can have a polymer coating having an anti-thrombogenic agent on the inner surface which directly contacts blood flow and a polymer coating having an anti-inflammatory agent on the outer surface which directly contacts blood vessel wall. The inner surface and the outer surface can be coated by the different methods. Also, there can be more than one coating on a surface. Furthermore, an entire surface of the medical device is not necessarily coated.

In the present invention, the coated structure or plate is ablated by a laser to form openings. The openings along with the remaining parts of the structure or plate make up the geometric pattern structure of the medical device. The structure or plate can be moved while the laser is held stationary to ablate the structure or plate into pattern, or alternatively, the laser can be programmed to move along a predetermined pattern by a method known to artisans. A combination of both, i.e. moving both the laser and the structure or plate, is also possible. In the present invention, even a coated stent having a complex stent pattern can be made with high precision. A medical devices having multiple coating layers and a complicated geometry pattern can also be easily manufactured by the method of the present invention without flaws such as polymer-bridges at gaps or corners. Also, the layer thickness can be easily controlled by the method of the present invention.

In the case where a plate is coated and ablated, the plate is formed into a portion of the medical device in the way known to artisans. In case the coated portion is a tube-like portion, it is formed by forming the flat plate into a tube-like shape and attaching the opposing edges of the plate together such as by fusing the two opposing sides. A method of fusing appropriate to a stent material can be chosen. Methods of fusing include fusing by heat or using adhesive.

After the ablation of the present invention, there is no need to polish the ablated medical device to avoid rough cut surface because of the high quality of the cut surface.

Furthermore, a plurality of medical devices can be manufactured by coating one large structure and, as ablating it as explained above, cutting the structure into individual coated portions. For example, if the coated portion is a tube-like portion, a long tubular structure is coated first, and then ablated, and then cut into individual tube-like portions of medical devices. Likewise, a large plate can be coated first, cut into a smaller plate, and then formed into an individual coated structure and ablated. Alternatively, a large coated plate can be shaped into a large coated structure, and then it is cut into individual coated structures as ablated. In this way, a plurality of medical devices be made by using one coating step. Also, all of the medical devices will have uniform coating thicknesses.

If necessary, the thickness of the coating can be easily measured before the ablation step. For example, it is very useful to know an amount of a biologically active material contained in a medical material. This amount can be calculated in the present invention by measuring the thickness of the coating after the coating is placed on the medical device. For example, based on the concentration of biologically active material in the coating composition, the thickness of the coating, the amount of biologically active material placed on the device can be determined.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

I claim:

1. A method for manufacturing a coated medical device having a coated portion having at least one opening therein, wherein the method comprises the steps of:
   (a) obtaining a metal structure having an inner surface and an outer surface;
   (b) coating at least a portion of the inner or outer surface of the structure with a first non-metallic coating material to form a coated structure; and
   (c) simultaneously ablating through the coating material and structure of the coated structure with an ultrashort-pulse laser to form at least one opening therein.

2. The method of claim 1, wherein the structure is a tubular structure.

3. The method of claim 1, wherein the medical device is a stent.

4. The method of claim 1, wherein step (b) comprises only coating the inner surface of the structure with the first coating material.

5. The method of claim 1, wherein step (b) comprises only coating the outer surface of the structure with the first coating material.

6. The method of claim 1, wherein step (b) comprises:
   (i) coating the inner surface of the structure with the first coating material and
   (ii) coating the outer surface of the structure with a second non-metallic coating material.

7. The method of claim 6, wherein the first coating material and the second coating material are the same.

8. The method of claim 1, wherein the first coating material is a coating composition and the surface is coated by dipping the surface into the coating composition.

9. The method of claim 1, wherein the first coating material is a coating composition and the surface is coated by spray-coating the coating composition onto the surface.

10. The method of claim 1, wherein the first coating material comprises a polymer and a biologically active material.

11. The method of claim 1, wherein the first coating material comprises a biologically active material, and the coating step (b) is conducted by immobilizing the first coating material onto at least a portion of the surface.

12. The method of claim 1, wherein the coated structure is ablated to form a plurality of openings therein that define a plurality of struts.

13. The method of claim 1, which further comprises cutting the coated structure into sections to form more than one coated portion.

14. The method of claim 13, wherein the cutting step is conducted between coating step and the ablating step.

15. A method for manufacturing a coated medical device having a coated portion having at least one opening therein, wherein the method comprises the steps of:
   (a) obtaining a metal plate having a first surface and a second surface;
   (b) coating at least a portion of the first surface or second surface with a first non-metallic coating material to form a coated plate;
   (c) simultaneously ablating through the coating material and plate of the coated plate with an ultrashort-pulse laser to form at least one opening therein; and
   (d) forming the coated plate into a tubular medical device.

16. The method of claim 15, which further comprises forming a tubular structure from the coated and ablated plate obtained in step (c).

17. The method of claim 15, wherein the medical device is a stent.

18. The method of claim 15, wherein step (b) comprises only coating the first surface of the plate with the first coating material.

19. The method of claim 15, wherein step (b) comprises only coating the second surface of the plate with the first coating material.

20. The method of claim 15, wherein step (b) comprises:
   (i) coating the first surface of the plate with the first coating material and
   (ii) coating the second surface of the plate with a second non-metallic coating material.

21. The method of claim 15, wherein the first coating material and the second coating material are the same.

22. The method of claim 15, wherein the first coating material is a coating composition and the surface is coated by dipping the surface into the coating composition.

23. The method of claim 15, wherein the first coating material is a coating composition and the surface is coated by spray-coating the coating composition onto the surface.

24. The method of claim 15, wherein the first coating material comprises a biologically active material, and coating is conducted by immobilizing the first coating material onto at least of a portion of the surface.

25. The method of claim 15, wherein the first coating material comprises a polymer and a biologically active material.

26. The method of claim 15, wherein the coated plate is ablated to form a plurality of openings therein that define a plurality of struts.

27. The method of claim 15, which further comprises cutting the coated plate into sections and forming more than one coated and ablated tubular structure.

28. The method of claim 27, wherein the cutting step is conducted between the coating step and the ablating step.

29. The method of claim 27, wherein the coated plate is cut as it is ablated.

30. A method for manufacturing a coated medical device having a coated portion having at least one opening therein, wherein the method comprises the steps of:
   (a) obtaining a metal structure having an inner surface and an outer surface;
   (b) coating at least a portion of the inner or outer surface of the structure with a first non-metallic coating material to form a coated structure; and
   (c) simultaneously ablating through the coating material and structure of the coated structure with a laser to form at least one opening therein.

31. A method for manufacturing a coated medical device having a coated portion having at least one opening therein, wherein the method comprises the steps of:
   (a) obtaining a metal plate having a first surface and a second surface;
   (b) coating at least a portion of the first surface or second surface of the plate with a first non-metallic coating material to form a coated plate;
   (c) simultaneously ablating through the coating material and plate of the coated plate with a laser to form at least one opening therein; and
   (d) forming the coated plate into a tubular medical device.

* * * * *

UNITED STATES PATENT AND TRADEMARK OFFICE
CERTIFICATE OF CORRECTION

PATENT NO. : 6,517,888 B1
DATED : February 11, 2003
INVENTOR(S) : Weber

It is certified that error appears in the above-identified patent and that said Letters Patent is hereby corrected as shown below:

<u>Title page,</u>
Item [75], the residence of the inventor, "Jan Weber", should be -- Maple Grove, Minnesota. --

Signed and Sealed this

Twenty-ninth Day of July, 2003

JAMES E. ROGAN
*Director of the United States Patent and Trademark Office*